United States Patent
Berlinger et al.

(10) Patent No.: US 10,872,427 B2
(45) Date of Patent: Dec. 22, 2020

(54) IMAGE GUIDED PATIENT SETUP FOR RADIOTHERAPY

(71) Applicant: Brainlab AG, Munich (DE)

(72) Inventors: Kajetan Berlinger, Munich (DE); Michael Stead, Unterhaching (DE)

(73) Assignee: BRAINLAB AG, Munich (DE)

(*) Notice: Subject to any disclaimer, the term of this patent is extended or adjusted under 35 U.S.C. 154(b) by 119 days.

(21) Appl. No.: 16/090,016

(22) PCT Filed: Feb. 23, 2018

(86) PCT No.: PCT/EP2018/054516
§ 371 (c)(1),
(2) Date: Sep. 28, 2018

(87) PCT Pub. No.: WO2018/154055
PCT Pub. Date: Aug. 30, 2018

(65) Prior Publication Data
US 2019/0156497 A1 May 23, 2019

Related U.S. Application Data

(63) Continuation-in-part of application No. PCT/EP2017/054323, filed on Feb. 24, 2017, and a
(Continued)

(51) Int. Cl.
*G06K 9/00* (2006.01)
*G06T 7/33* (2017.01)
(Continued)

(52) U.S. Cl.
CPC .............. *G06T 7/33* (2017.01); *A61B 5/0077* (2013.01); *A61B 5/7292* (2013.01); *A61B 34/10* (2016.02);
(Continued)

(58) Field of Classification Search
CPC . G06T 2207/10081; G06T 2207/20128; G06T 2207/20221; G06T 2207/30196;
(Continued)

(56) References Cited

U.S. PATENT DOCUMENTS 7,720,196 B2 5/2010 Zhang et al.
2009/0187112 A1* 7/2009 Meir ....................... G06T 7/593
600/534

(Continued)

FOREIGN PATENT DOCUMENTS

EP 2239010 B1 6/2013
WO WO2013009427 A2 1/2013

OTHER PUBLICATIONS

Gerben et al ("Clinical Results of image-Guided Deep Inspiration Breath Hold Breast Irradiation", Int. J. Radiation Oncology Biol. Phys., vol. 78, No. 5, pp. 1345-1351, 2010, Science direct (Year: 2010).*

(Continued)

*Primary Examiner* — Amara Abdi
(74) *Attorney, Agent, or Firm* — Middleton Reutlinger (57) ABSTRACT

The present invention relates to a method for setting up a patient for radiotherapy, wherein the patient is scanned prior to therapy in both, a free-breathing state and a DIBH-state for which the patient performs a so-called "deep inspiration breath-hold". The obtained data is registered to a CT-dataset which forms the basis for a treatment plan. The patient is then set up with respect to a radiation treatment apparatus based on the data obtained for the free-breathing state.

15 Claims, 2 Drawing Sheets

Related U.S. Application Data continuation-in-part of application No. PCT/EP2018/053100, filed on Feb. 7, 2018.

(51) Int. Cl.

| | | |
|---|---|---|
| *G06T 7/30* | (2017.01) | |
| *G06T 7/73* | (2017.01) | |
| *G06T 7/246* | (2017.01) | |
| *A61B 5/00* | (2006.01) | |
| *A61N 5/10* | (2006.01) | |
| *A61B 34/10* | (2016.01) | |
| *G16H 30/40* | (2018.01) | |
| *G06T 7/00* | (2017.01) | |
| *G06T 11/00* | (2006.01) | |
| *A61B 90/00* | (2016.01) | |

(52) U.S. Cl.
CPC ......... *A61N 5/1037* (2013.01); *A61N 5/1039* (2013.01); *A61N 5/1049* (2013.01); *G06T 7/0014* (2013.01); *G06T 7/248* (2017.01); *G06T 7/251* (2017.01); *G06T 7/30* (2017.01); *G06T 7/74* (2017.01); *G06T 7/75* (2017.01); *G06T 11/003* (2013.01); *G16H 30/40* (2018.01); *A61B 2034/107* (2016.02); *A61B 2090/3762* (2016.02); *A61N 2005/1059* (2013.01); *G06T 2207/10072* (2013.01); *G06T 2207/10081* (2013.01); *G06T 2207/10116* (2013.01); *G06T 2207/20128* (2013.01); *G06T 2207/20221* (2013.01); *G06T 2207/30008* (2013.01); *G06T 2207/30081* (2013.01); *G06T 2207/30096* (2013.01); *G06T 2207/30196* (2013.01)

(58) Field of Classification Search
CPC . G06T 2207/10072; G06T 2207/30008; G06T 2207/30081; G06T 2207/10116; G06T 2207/30096; G06T 7/33; G06T 7/74; G06T 7/75; G06T 7/251; G06T 7/248; G06T 7/30; G06T 7/0014; G06T 11/003; A61B 5/0077; A61B 5/7292; A61B 34/10; A61B 2034/107; A61B 2090/3762; A61N 5/1037; A61N 5/1039; A61N 5/1049; A61N 2005/1059; G16H 30/40
See application file for complete search history.

(56) References Cited

U.S. PATENT DOCUMENTS

| | | | | |
|---|---|---|---|---|
| 2010/0202673 | A1* | 8/2010 | Zhang | A61B 6/466 382/128 |
| 2012/0106704 | A1* | 5/2012 | Maurer, Jr. | A61N 5/1077 378/65 |
| 2013/0287167 | A1 | 10/2013 | Gum et al. | |
| 2015/0302608 | A1 | 10/2015 | Vilsmeier et al. | |
| 2016/0016009 | A1* | 1/2016 | Manzke | A61N 5/1065 382/132 |
| 2017/0340297 | A1* | 11/2017 | Varkuti | A61B 6/0492 |

OTHER PUBLICATIONS

Xing et al. "Overview of Image-Guided Radiation Therapy". Medical Dosim, Vo. 31, No. 2. May 9, 2006.

Mittauer et al. "Monitoring ABC-assisted deep inspiration breath hold for left-sided breast radiotherapy with an optical tracking system" Medical Physics, vol. 42, No. 1. Jan. 1, 2015.

D'Souza et al. "Real-time intra-fraction-motion tracking using the treatment couch: a feasibility study; Couch-based motion synchronized radiation delivery" Physics in Medicine and Biology, Vo. 50. No. 17. Sep. 7, 2005.

Nehmeh et al. "Deep-Inspriation Breath-Hold PET/CT of the Thorax" The Journal of Nuclear Medicine. Jan. 1, 2007.

Gikas et al. "Deep inspiration breath hold and respiratory gating strategies for reducing organ motion in radiation treatment" Seminars in Radiation Onco, vol. 14, No. 1. Jan. 1, 2004.

Borst et al. "Clinical Results of Image-Guided Deep Inspiration Breath Hold Breast Irradiation" International Journal of Radiation: Oncology Biology Physics, Pergamon Press. vol. 78, No. 5. Dec. 1, 2010.

Wong et al. "Real-Time Monitoring and Control on Deep Inspiration Breath-Hold for Lung Cancer Radiotherapy-Combination of ABC and External Marker Tracking" Medical Physics. vol. 37, No. 9. Aug. 16, 2010.

Gardner et al. "Tumor Localization, Disimetry, Simulation and Treatment Procedures in Radiotherapy: the Isocentric Technique" Department of Radiology, Stanford University of Medicine. Jan. 1, 1972.

International Search Report and Written Opinion issued in Application No. PCT/EP2018/054516 dated Apr. 20, 2018.

Latty et al. "Review of Deep Inspiration Breath-Hold Techniques for the Treatment of Breast Cancer" Journal of Medical Radiation Sciences. Jan. 12, 2015.

\* cited by examiner

IMAGE GUIDED PATIENT SETUP FOR RADIOTHERAPY

FIELD OF THE INVENTION

The present invention relates to a computer-implemented method for setting up a patient for radiotherapy, a corresponding computer program, a non-transitory program storage medium storing such a program and a computer for executing the program, as well as a medical system comprising an electronic data storage device and the aforementioned computer.

TECHNICAL BACKGROUND

For medical procedures performed on a patient, such as image guided surgery, radiotherapy or even image based diagnostics it is desirable to know the spatial position (including the spatial location and/or the spatial orientation), and preferably even the size and the shape of anatomical structures of interest of the patient's body. While some anatomical structures maintain their position over time, some structures do not as they are subject to the patient's respiratory motion. The problem which arises in this context is that some medical procedures are planned on the basis of images that show certain anatomical structures of interest, but which have been acquired prior to the actual medical procedure. Thus, it has to be ensured that the anatomical structures of interest are arranged in the same manner for the medical procedure, as they were when the planning image was acquired.

Radiotherapy of breast cancer as a particular example of such medical procedures starts in most cases with a resection of the tumor, which is then followed by the actual radiation therapy. Clinical studies have shown that irradiating the tumor bed reduces the risk of recurrence dramatically.

As the heart, especially the RIVA (Ramus interventricularis anterior) is very sensitive to radiation, such that unintended irradiation of the heart may yield in the long term to heart diseases, special care has to be taken to safe the heart from radiation. This problem particularly arises for treatment of the left breast, as the distance from the radiotherapy target to the heart is comparatively short. Therefore, most procedures are planned and performed in the state of a so-called "DIBH" (deep inspiration breath-hold). With an increased inspiration the heart moves away from the radiotherapy target in an inferior and posterior direction, and therefore moves out of the radiation beam's path. The patient is coached to perform a DIBH during a pre-therapy CT-scan, on which basis the treatment plan is created. During the following treatment, the patient is again coached to reproduce the DIBH as close as possible to the one that was existent when the CT-scan was made. In order to verify that the DIBH is performed correctly during treatment, medical personnel manually checks the position of the anatomical structures of interest on X-ray-images or EPID-images that are acquired during the treatment-DIBH.

The present invention has the object of providing a fast and easy patient setup that precisely places a pathological target structure at a desired position with respect to a radiation treatment apparatus.

The present invention can be used for radiotherapy procedures e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention relates to a method for setting up a patient for radiotherapy, wherein the patient is scanned prior to therapy in both, a free-breathing state and a DIBH-state for which the patient performs a so-called "deep inspiration breath-hold". The obtained data is registered to a CT-dataset which forms the basis for a treatment plan. The patient is then set up with respect to a radiation treatment apparatus based on the data obtained for the free-breathing state.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method for setting up a patient for radiotherapy. The method comprises executing, on at least one processor of at least one computer (for example at least one computer being part of the navigation system), the following exemplary steps which are executed by the at least one processor:

a) free-breathing data is acquired, describing a spatial position of a reference structure of the patient in a free-breathing state, particularly wherein the free-breathing data describes an time-averaged spatial position of the reference structure;
b) DIBH data is acquired, describing an image dataset of the patient in a DIBH state, showing at least the reference structure and a target structure of the patient, which is to be irradiated;
c) registration data is determined based on the free-breathing data and the DIBH data, describing a spatial correspondence between the reference structure in the free-breathing state and the target structure in the DIBH-state;
d) isocentre data is acquired, describing the spatial position of an isocentre of a radiation treatment apparatus;
e) positioning data is determined based on the registration data and the isocentre data, describing a spatial position of the reference structure in the free-breathing state, for which a spatial position of the target structure in the corresponding DIBH-state conforms with the spatial position of the isocentre of the radiation treatment apparatus.

The first method step is performed prior to treatment and during a planning phase, and is to determine the spatial position of a reference structure of the patient's anatomy, on the basis of which the patient is later positioned with respect to a radiation treatment apparatus. Such reference structure can be any anatomical structure that moves due to the respiratory motion of the patient and is therefore applicable to monitor the breathing motion of the patient. For example, the reference structure can be the outer contour of the patient's body, specifically of the patient's chest or any part thereof. In particular, the sternum or a section thereof can represent the reference structure. Further, it is necessary that the spatial position of the reference structure is determined in a state of the patient which will prevail when the patient is positioned with respect to the radiation treatment apparatus at a later point in time. For example, this state can be a free-breathing state, when the patient who is lying on a patient couch is breathing calmly and the respiratory motion is rather shallow. Since the reference structure still moves in accordance with the patient's respiration, it's spatial position may be tracked over a certain period of time, so that a time-averaged mean position can be calculated that represents the overall position of the reference structure. However, a single image "shot" of the reference structure is expected to be sufficiently accurate for the inventive approach, since the respiratory motion is almost neglectable as compared to the motion performed for a DIBH. For example, the reference structure's spatial position can be determined with the help of a CT-imaging procedure outputting images that show the reference structure.

Further, the inventive method involves the step of acquiring the spatial position of this reference structure in a DIBH-state of the patient, i.e. a state for which the patient takes a trained posture and holds a rather deep breath. This could be done in a manner quite similar to the first step, for example by creating a second CT-dataset showing the reference structure for the DIBH-state. For example, the second reference structure position for the DIBH-state could be determined on the basis of a planning-CT-dataset. In that case, the reference structure's position with respect to a pathological anatomical structure to be irradiated later on can be directly taken from that dataset. In such case a separate registration step is not necessary.

Once the reference structures positions for both, a free-breathing state and a DIBH-state are determined, the images or datasets that show the respective positions have to be registered with each other and with respect to the planning-CT-dataset.

For such registration, any applicable registration methods are conceivable. For example, a rigid or elastic image fusion may be performed on the basis of one or more anatomical structures shown in the respective images/datasets. Specifically, such image fusion can be based on one or more anatomical structures that do not significantly move due to the patient's respiratory motion, for example the patient's spine or any section and/or vertebrae thereof.

Additionally or alternatively, the images/datasets to be registered with each other can be acquired in one and the same co-ordinate system. Thus, with a patient that does not significantly move, or does not move at all, such registration would be superfluous.

The output of such registration is the spatial correspondence between the reference structure in the free-breathing state of the patient, and the target structure in the DIBH-state of the patient. In other words, this correspondence describes the spatial position of the target structure in the DIBH-state as a function of the spatial position of the reference structure in the free-breathing state of the patient, or vice versa.

Further, it is necessary to know the spatial position of the isocentre of the radiation treatment apparatus, in which the patient's pathological structure has to be placed in during a later radiotherapy procedure.

With the data acquired/determined so far, it is possible to determine at which position the reference structure of a free-breathing patient has to be placed with respect to the machine's isocentre, such that, when the positioned patient performs a DIBH, the target structure (e.g. a breast tumour to be treated) will come to rest precisely in the isocentre of the radiation treatment apparatus.

Consequently, the present invention provides an approach which allows placing the patient with respect to a radiation treatment apparatus primarily based on the tracked position of a reference structure of a free-breathing patient.

An example of the present invention allows to place the patient in an "intermediate"-position, i.e. in a position not ready for radiotherapy yet, but in a position that is offset therefrom and allows for a convenient access to the patient. For example, medical personnel may need to manually help the patient in taking a posture that is beneficial for the medical outcome of the treatment procedure. Since during radiotherapy the patient is positioned at an increased height, such patient interaction is often inconvenient, if not impossible. Therefore, the present invention may provide for a lower intermediate position the patient can be positioned in before being transferred to an ultimate position ready for treatment.

In a further example, camera data is acquired, describing a current spatial position of the reference structure of the patient in the free-breathing state and/or the DIBH-state, particularly with respect to the radiation treatment apparatus. In other words, the patient's reference structure can be tracked with the help of one or more cameras while the patient is positioned with respect to the radiation treatment apparatus.

This may involve acquiring at least one monoscopic camera image or at least one stereoscopic camera image pair of the reference structure of the patient by at least one camera or camera arrangement. This one or more camera(s) are susceptible to visible light and/or to infrared light and therefore deliver visible-light images and/or thermal images. Moreover, a structured-light-pattern, for example a light-grid is projected onto a region the reference structure lies in, which facilitates determining the three-dimensional shape of the patient's outer contour.

With all the data acquired and determined so far, control data can be determined and particularly output, so as to control the operation of a medical device such that the current spatial position of the reference structure as described by the camera data conforms with the spatial position of the reference structure as described by one of the positioning data or the intermediate positioning data, respectively. In other words, the current position of the reference structure which is tracked by the at least one visible-light-camera(s) and/or thermal-camera(s) is aligned with the calculated position the reference structure has to be placed in such that the target structure comes to rest in the machine isocentre when the patient performs a DIBH. For example, the patient can be moved by a motorised patient couch, which can further be movable in 6 degrees of freedom.

Further, it can be checked whether the patient performs a DIBH correctly after being positioned for radiotherapy by acquiring X-ray-images. For example, at least one monoscopic X-ray-image, particularly at least one stereoscopic X-ray-image-pair is acquired in the DIBH-state of the patient, i.e. when the patient performs a DIBH. On the basis of the acquired X-ray-images which show the target structure, it can be determined whether this target structure actually lies within the known isocentre position when the DIBH is performed. Further, a threshold may be defined for the relative position between the target structure in the DIBH-state and the isocentre, such that small positional deviations of the target structure with respect to the isocentre are still acceptable for radiotherapy. Moreover, the acquired X-ray-images allow for checking whether further anatomical structures are positioned as expected during the planning phase. For example, the heart of the patient must not lie within a radiation beam path and the patient should not lift the spine when performing a DIBH.

If such predefined criteria are met, the spatial position of the reference structure as described by the free-breathing data and/or the DIBH-data can be replaced by a current spatial position of the reference structure of the patient in the free-beathing state and/or the DIBH-state, respectively. As described by the camera data, particularly wherein the camera data is updated on a regular basis for subsequent DIBH-states of the patient and/or a later treatment session. In other words, the images/datasets and the positions of anatomical structures derived therefrom are replaced by images/datasets obtained from the one or more cameras which are more up-to-date, thereby following a "latest is greatest"-approach. This applies to the images/datasets acquired during a planning phase before the patient was positioned with respect to the radiation treatment apparatus, and to foregoing images/datasets acquired via the one or more cameras during the treatment phase. Thus, the patient position and posture with respect to the radiation treatment apparatus can be monitored to keep the treatment setup up-to-date. Further, the latest acceptable image/dataset can be stored to be used for positioning the patient for a later treatment session that may occur even days later.

On the other hand, however, if the X-ray-images show that the target structure is not satisfactorily placed with respect to the isocentre, the positional data derived from the X-ray-images may help in repositioning the patient with respect to the radiation treatment apparatus, for example by moving the patient couch to a corrected position.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
a) the at least one computer according to the fourth aspect;
b) at least one electronic data storage device storing at least the free-breathing data and the DIBH data; and
c) a medical device for carrying out a medical procedure on the patient,
wherein the at least one computer is operably coupled to
the at least one electronic data storage device for acquiring, from the at least one data storage device, at least the free-breathing data and the DIBH data, and
the medical device for issuing a control signal to the medical device for controlling the operation of the medical device on the basis of the control data.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling, on the basis of the control data.

The invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to setting up a patient. For this reason alone, no surgical or therapeutic activity and in particular no surgical or therapeutic step is necessitated or implied by carrying out the invention.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/health-care_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
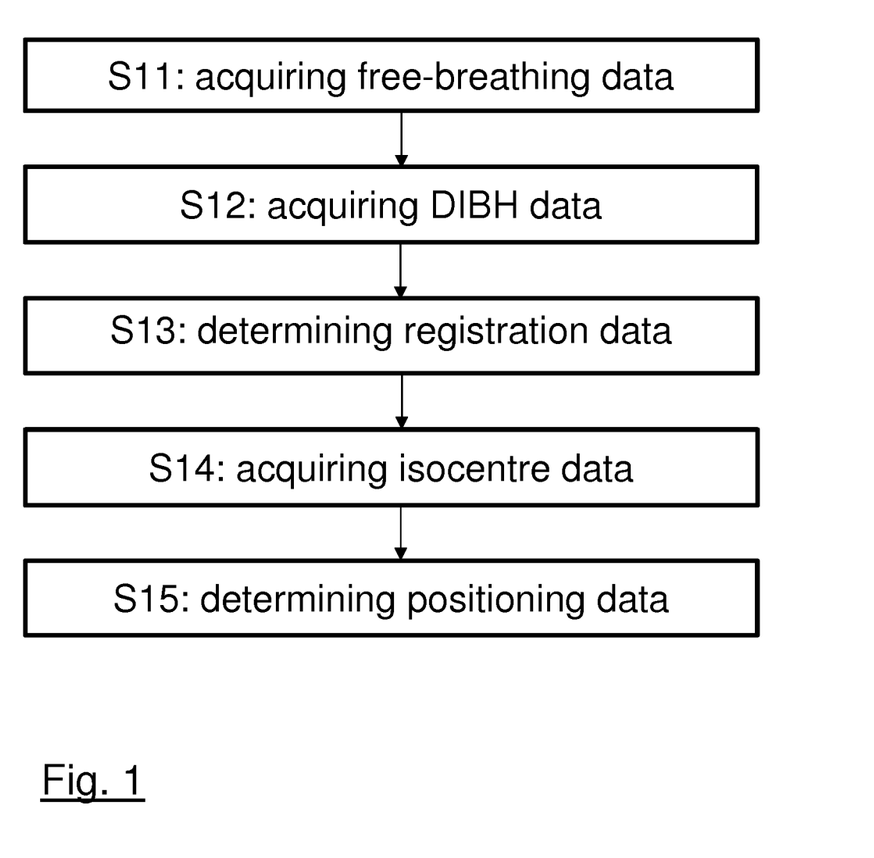
FIG. 1 illustrates the basic steps of the method according to the first aspect of the present invention.

FIG. 1 illustrates the basic steps of the method according to the first aspect of the present invention. In a first step S11, the spatial position of a reference structure, for example the sternum of a patient is determined for a freely breathing patient. Additionally, the spatial position of that reference structure is determined (step S12), when the patient performs a DIBH, wherein this position can be directly derived from a planning-CT-dataset for which the patient has to perform a DIBH anyhow. The positional data of the reference structure is, if necessary, then registered with the planning-CT-dataset (step S13), which shows for a DIBH-state of the patient not only the pathological target structure (e.g. a breast tumour) to be irradiated, but also the reference structure.

As soon as the spatial position of the machine isocentre is known (step S14) a spatial position can be calculated (step S15), in which the reference structure of a freely breathing patient has to be placed with respect to the radiation treatment apparatus, such that when the patient performs a DIBH, the target structure comes to rest in the isocentre of the radiation treatment apparatus.

Figure 2:
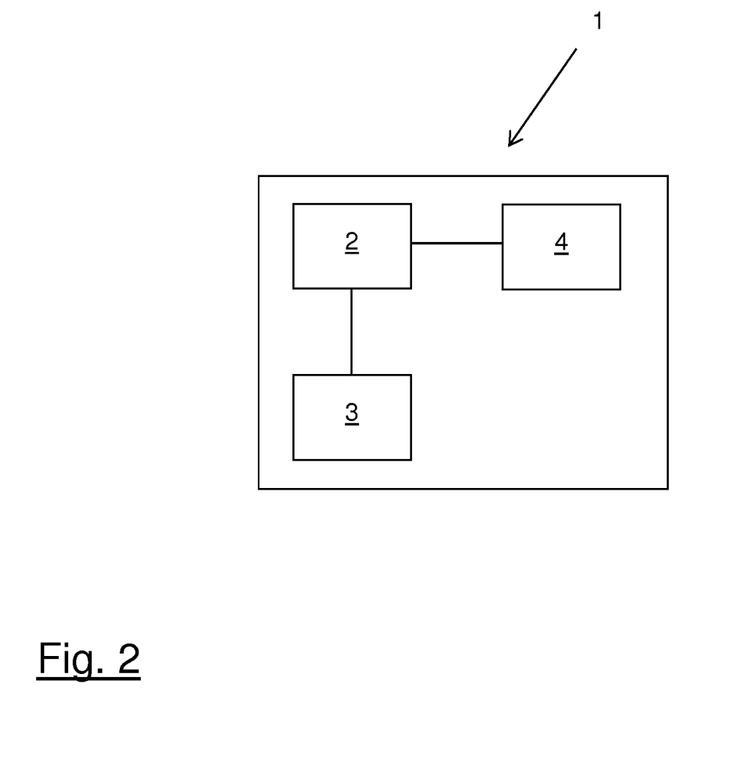
FIG. 2 is a schematic illustration of the system according to the fifth aspect.

FIG. 2 is a schematic illustration of the medical system 1 according to the fifth aspect. The system is in its entirety identified by reference sign 1 and comprises a computer 2, an electronic data storage device (such as a hard disc) 3 for storing at least the patient data and a medical device 4 (such as a radiation treatment apparatus). The components of the medical system 1 have the functionalities and properties explained above with regard to the fifth aspect of this disclosure.

The invention claimed is:

1. A computer-implemented method for setting up a patient for radiotherapy, the method comprising:
    acquiring free-breathing data describing a spatial position of a reference structure of the patient in a free-breathing state;
    acquiring deep-inspiration-breath-hold data describing an image dataset of the patient in a state of a deep-inspiration-breath-hold, showing at least the reference structure and a target structure of the patient, which is to be irradiated;
    determining registration data based on the free-breathing data and the deep-inspiration-breath-hold data, describing the spatial position of the target structure in the state of the deep-inspiration-breath-hold as a function of the spatial position of the reference structure in the free-breathing state;
    acquiring isocentre data describing the spatial position of an isocentre of a radiation treatment apparatus;
    determining positioning data based on the registration data and the isocentre data, describing a spatial position of the reference structure in the free-breathing state, for which a spatial position of the target structure in the corresponding state of the deep-inspiration-breath-hold conforms with the spatial position of the isocentre of the radiation treatment apparatus.

2. The method according to claim 1, wherein acquiring free-breathing data and/or acquiring deep-inspiration-breath-hold data involves acquiring a CT-dataset of the patient.

3. The method according to claim 1, wherein determining registration data involves an image fusion of at least one anatomical structure described in both, the free-breathing data and the deep-inspiration-breath-hold data, particularly of at least one anatomical structure the spatial position of which does not significantly change due to the patient's respiratory motion.

4. The method according to claim 1, wherein the free-breathing data and the deep-inspiration-breath-hold data is acquired within the same co-ordinate system.

5. The method according to claim 1, wherein the reference structure is represented by
    an outer contour of the patient's body, or a section thereof; or
    the sternum of the patient, or a section thereof;
and/or wherein an anatomical structure used for image fusion is represented by
    the spine of the patient, or a section thereof;
and/or wherein the target structure is represented by
    a breast tumour of the patient, or a section thereof.

6. The method according to claim 1, further including determining intermediate positioning data based on the registration data and the isocentre data, describing a spatial position of the reference structure in the free-breathing state, which is offset vertically downwards from the spatial position of the reference structure in the free-breathing state for which a spatial position of the target structure in the state of the deep-inspiration-breath-hold conforms with the spatial position of the isocentre of the radiation treatment apparatus.

7. The method according to claim 1, further including acquiring camera data describing a current spatial position of the reference structure of the patient in the free-breathing state and/or the state of the deep-inspiration-breath-hold, particularly with respect to the radiation treatment apparatus.

8. The method according to claim 7, wherein acquiring camera data involves acquiring at least one monoscopic/stereoscopic camera image of the reference structure of the patient, by at least one camera susceptible to visible light and/or infrared light, particularly wherein a structured-light-pattern is projected onto the reference structure of the patient, wherein the at least one monoscopic/stereoscopic camera image comprises at least one visible-light image and/or at least one thermal image.

9. The method according to claim 1 further including determining control data output, based on the camera data and one of the positioning data and the intermediate positioning data, the control data output operable to control the operation of a medical device such that the current spatial position of the reference structure as described by the camera data conforms with the spatial position of the reference structure as described by one of the positioning data or the intermediate positioning data, respectively.

10. The method according to claim 1, wherein, with the current spatial position of the reference structure conforming with the spatial position of the reference structure as described by the positioning data, at least one monoscopic X-ray-image, particularly at least one stereoscopic X-ray-image-pair is acquired in the state of the deep-inspiration-breath-hold, wherein it is determined on the basis of the at least one acquired monoscopic X-ray-image and the isocentre data whether the relative position of the target structure in the state of the deep-inspiration-breath-hold and the isocentre of the radiation treatment apparatus is within a predefined threshold for acceptance.

11. The method according to claim 10, wherein, if predefined criteria for spatial positions of anatomical structures are met, including an acceptable relative position of the target structure in the state of the deep-inspiration-breath-hold and the isocentre, the spatial position of the reference structure described by the free-breathing data and/or the deep-inspiration-breath-hold data is replaced by a current spatial position of the reference structure of the patient in the free-breathing state and/or the state of the deep-inspiration-breath-hold, respectively, as described by the camera data, particularly wherein the camera data is updated on a regular basis for subsequent states of the deep-inspiration-breath-hold of the patient and/or a later treatment session.

12. The method according to claim 9, wherein, if predefined criteria for spatial positions of anatomical structures are not met, including an acceptable relative position of the target structure in the state of the deep-inspiration-breath-hold and the isocentre, control data is determined and particularly output on the basis of the at least one acquired monoscopic X-ray-image and the isocentre data, the control data being adapted to control the operation of the medical device such that the position of the target structure in the state of the deep-inspiration-breath-hold and the isocentre of the radiation treatment apparatus is within a predefined threshold for acceptance.

13. A non-transitory computer-readable storage medium storing a computer program which, when executed on at least one processor of at least one computer, causes the at least one computer to perform the steps of:

acquiring free-breathing data describing a spatial position of a reference structure of the patient in a free-breathing state, wherein the free-breathing data describes a time-averaged spatial position of the reference structure;

acquiring deep-inspiration-breath-hold data describing an image dataset of the patient in a state of a deep-inspiration-breath-hold, showing at least the reference structure and a target structure of the patient, which is to be irradiated;

determining registration data based on the free-breathing data and the deep-inspiration-breath-hold data, describing the spatial position of the target structure in the state of the deep-inspiration-breath-hold as a function of the spatial position of the reference structure in the free-breathing state;

acquiring isocentre data describing the spatial position of an isocentre of a radiation treatment apparatus;

determining positioning data based on the registration data and the isocentre data, describing a spatial position of the reference structure in the free-breathing state, for which a spatial position of the target structure in the corresponding state of the deep-inspiration-breath-hold conforms with the spatial position of the isocentre of the radiation treatment apparatus.

14. A medical system for setting up a patient for radiotherapy, comprising:
at least one processor having associated memory with program instructions, the instructions, when executed, operable to:
acquire free-breathing data describing a spatial position of a reference structure of the patient in a free-breathing state;
acquire deep-inspiration-breath-hold data describing an image dataset of the patient in a state of a deep-inspiration-breath-hold, showing at least the reference structure and a target structure of the patient, which is to be irradiated;
determine registration data based on the free-breathing data and the deep-inspiration-breath-hold data, describing the spatial position of the target structure in the state of the deep-inspiration-breath-hold as a function of the spatial position of the reference structure in the free-breathing state;
acquiring isocentre data describing the spatial position of an isocentre of a radiation treatment apparatus;
determine positioning data based on the registration data and the isocentre data, describing a spatial position of the reference structure in the free-breathing state, for which a spatial position of the target structure in the corresponding state of the deep-inspiration-breath-hold conforms with the spatial position of the isocentre of the radiation treatment apparatus;
at least one electronic data storage device associated with the at least one processor and storing at least the free-breathing data and the deep-inspiration-breath-hold data;
a medical device for carrying out a medical procedure on the patient; and
wherein the at least one processor is operably coupled to the medical device for issuing a control signal to the medical device for controlling the operation of the medical device on the basis of the control data output.

15. The system according to the claim 14, wherein the medical device comprises:
a radiation treatment apparatus comprising a treatment beam source and a patient support unit,
wherein the at least one processor is operably coupled to the radiation treatment apparatus for issuing the control signal to the radiation treatment apparatus for controlling, on the basis of the control data, at least one of:
the operation of the treatment beam source or
the position of the patient support unit.

* * * * *